(12) United States Patent
Mehta

(10) Patent No.: US 9,642,561 B2
(45) Date of Patent: *May 9, 2017

(54) EXPANDABLE SURGICAL INSTRUMENTS AND METHODS OF USE AND FABRICATION

(71) Applicant: KYPHON SARL, Neuchatel (CH)

(72) Inventor: Ankit K. Mehta, Santa Clara, CA (US)

(73) Assignee: Kyphon Sàrl, Neuchâtel (CH)

(*) Notice: Subject to any disclaimer, the term of this patent is extended or adjusted under 35 U.S.C. 154(b) by 0 days.

This patent is subject to a terminal disclaimer.

(21) Appl. No.: 14/614,083

(22) Filed: Feb. 4, 2015

(65) Prior Publication Data

US 2015/0150489 A1   Jun. 4, 2015

Related U.S. Application Data

(62) Division of application No. 12/841,924, filed on Jul. 22, 2010, now Pat. No. 8,979,863.

(51) Int. Cl.
| A61B 19/00 | (2006.01) |
| A61B 5/00 | (2006.01) |
| A61B 5/107 | (2006.01) |
| A61B 17/02 | (2006.01) |
| A61B 90/00 | (2016.01) |
| A61B 17/00 | (2006.01) |

(52) U.S. Cl.
CPC .......... *A61B 5/1076* (2013.01); *A61B 5/4566* (2013.01); *A61B 17/025* (2013.01); *A61B 90/06* (2016.02); *A61B 2017/00557* (2013.01); *A61B 2017/0256* (2013.01); *A61B 2090/061* (2016.02)

(58) Field of Classification Search
CPC ... A61B 5/1076; A61B 5/4566; A61B 17/025; A61B 2017/00557
See application file for complete search history.

(56) References Cited

U.S. PATENT DOCUMENTS

| 1,054,802 | A | * | 3/1913 | Spiro | A61B 5/1076 600/588 |
| 5,045,061 | A | * | 9/1991 | Seifert | A61M 25/09 600/585 |
| 5,810,867 | A | * | 9/1998 | Zarbatany | A61M 25/0054 604/96.01 |
| 5,868,735 | A | * | 2/1999 | Lafontaine | A61B 18/02 606/21 |
| 6,231,543 | B1 | * | 5/2001 | Hegde | A61M 25/10 604/96.01 |
| 6,280,411 | B1 | * | 8/2001 | Lennox | A61L 29/085 604/103.01 |
| 6,375,637 | B1 | * | 4/2002 | Campbell | A61M 25/10 604/103 |
| 6,500,132 | B1 | * | 12/2002 | Li | A61B 5/1076 128/898 |
| 7,182,773 | B2 | * | 2/2007 | Bouchier | A61B 5/1076 606/192 |

(Continued)

*Primary Examiner* — Christian Sevilla

(57) ABSTRACT

A system for assessing an intervertebral disc space comprises an elongated catheter with proximal and distal ends and an expandable body attached to the distal end of the elongated catheter. The expandable body includes proximal and distal end portions. The system further comprises a securing mechanism encircling at least one of the proximal or distal end portions of the expandable body to tighten the expandable body against the elongated catheter.

20 Claims, 4 Drawing Sheets

(56) References Cited

U.S. PATENT DOCUMENTS

| | | | |
|---|---|---|---|
| 7,241,297 B2 | 7/2007 | Shaolian et al. | |
| 7,637,886 B2 * | 12/2009 | Herweck | A61L 29/041 604/103.01 |
| 7,722,624 B2 | 5/2010 | Boucher et al. | |
| 7,892,201 B1 * | 2/2011 | Laguna | A61M 25/10 604/96.01 |
| 8,043,296 B2 * | 10/2011 | Chasmawala | A61B 17/8855 606/90 |
| 8,636,690 B2 * | 1/2014 | Alpini | A61M 25/1002 604/101.05 |
| 8,979,863 B2 * | 3/2015 | Mehta | A61B 17/025 606/102 |
| 2008/0161825 A1 * | 7/2008 | Greenhalgh | A61B 5/1076 606/102 |
| 2008/0194996 A1 * | 8/2008 | Kassab | A61B 5/053 600/593 |
| 2008/0200871 A1 * | 8/2008 | Slater | A61M 25/0097 604/96.01 |
| 2009/0275890 A1 | 11/2009 | Leibowitz et al. | |
| 2009/0276048 A1 * | 11/2009 | Chirico | A61B 17/025 623/17.11 |
| 2011/0172596 A1 | 7/2011 | Auyoung et al. | |
| 2012/0022571 A1 * | 1/2012 | Mehta | A61B 17/025 606/192 |
| 2012/0022574 A1 * | 1/2012 | Mafi | A61M 25/10 606/198 |
| 2012/0259238 A1 * | 10/2012 | Gunday | A61B 5/6853 600/547 |

\* cited by examiner

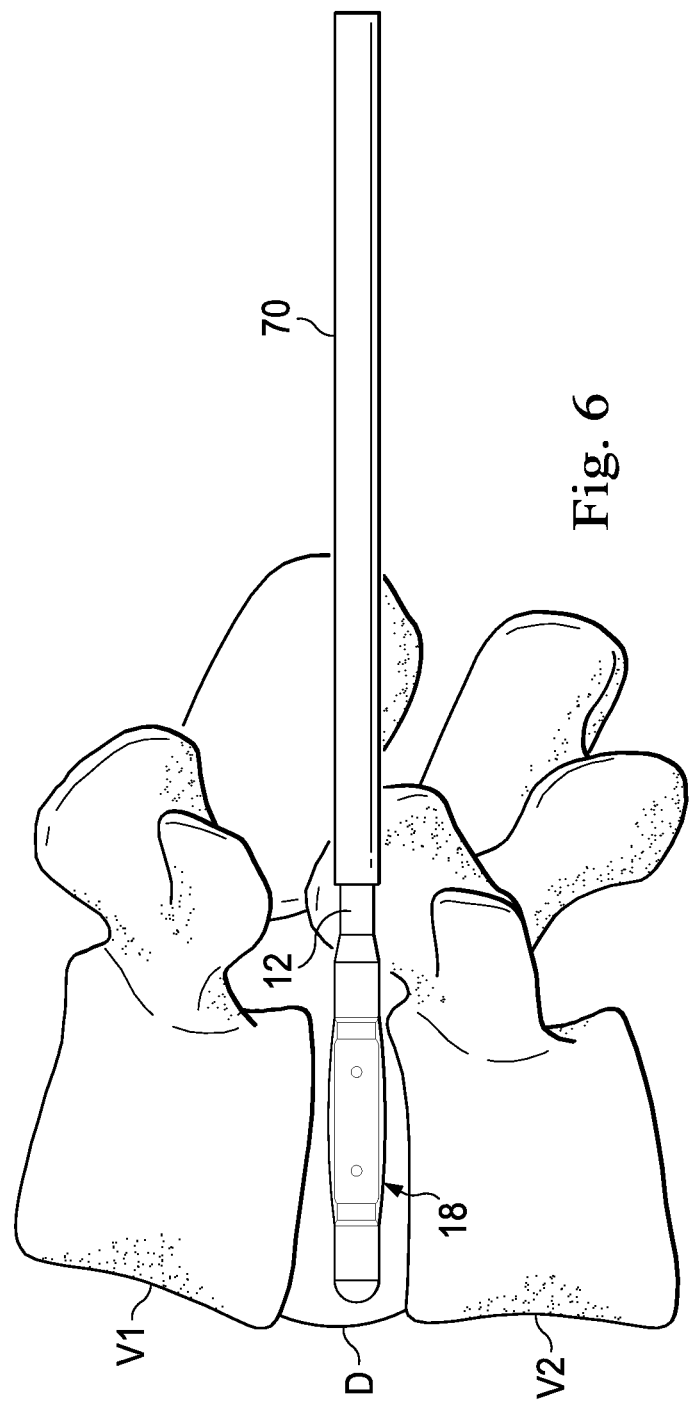

EXPANDABLE SURGICAL INSTRUMENTS AND METHODS OF USE AND FABRICATION

CROSS-REFERENCE TO RELATED APPLICATIONS

This application is a continuation application of U.S. patent application Ser. No. 12/841,924, filed on Jul. 22, 2010, which is incorporated herein by reference herein, in its entirety.

BACKGROUND

Degenerated disc disease refers to a syndrome in which a compromised disc causes low back pain. Disc degeneration may result in disc herniation in which the central portion of the intervertebral disc, known as the nucleus pulposus, may protrude through an opening in the surrounding fibrous ring, known as the annulus fibrous. A herniated lumbar disc can push on spinal nerves causing severe, shooting, leg pain, numbness, and/or weakness. Discectomy is a surgical procedure in which the nucleus pulposus of a herniated intervertebral disc is resected or removed to relieve pressure on the spinal cord and radiating nerves. Improved tools are needed to allow physicians to evaluate the extent of discectomy that has been performed and to assess the intradiscal space for further procedures such as fusion or arthroplasty.

SUMMARY

In one embodiment of the present disclosure, a system for assessing an intervertebral disc space comprises an elongated catheter with proximal and distal ends and an expandable body attached to the distal end of the elongated catheter. The expandable body includes proximal and distal end portions. The system further comprises a securing mechanism encircling at least one of the proximal or distal end portions of the expandable body to tighten the expandable body against the elongated catheter.

In another embodiment of the present disclosure, a method for assessing an intervertebral disc space comprises selecting an assessment instrument including an elongated catheter with proximal and distal ends and an expandable body attached to the distal end of the elongated catheter. The expandable body includes proximal and distal end portions. The securing mechanism encircles at least one of the proximal or distal end portions of the expandable body to tighten the expandable body against the elongated catheter. The method further includes inserting the expandable body into the intervertebral disc space and expanding the expandable body within the intervertebral disc space.

In another embodiment of the present disclosure, a system for assessing an intervertebral disc space comprises an elongated catheter with proximal and distal sections and an expandable tube with proximal and distal ends. The distal end is attached to the distal section of the elongated catheter and the proximal end is attached to the elongated catheter between the proximal and distal sections. The system further includes a securing mechanism encircling at least one of the proximal or distal ends of the expandable tube and overlapping the at least one proximal or distal end and the elongated catheter to tighten the expandable body against the elongated catheter.

Further aspects, forms, embodiments, objects, features, benefits, and advantages of the present invention shall become apparent from the detailed drawings and descriptions provided herein.

BRIEF DESCRIPTION OF THE DRAWINGS

FIG. 6 illustrates deployment of a medical device according to an embodiment of this disclosure.

DETAILED DESCRIPTION

Figure 1:
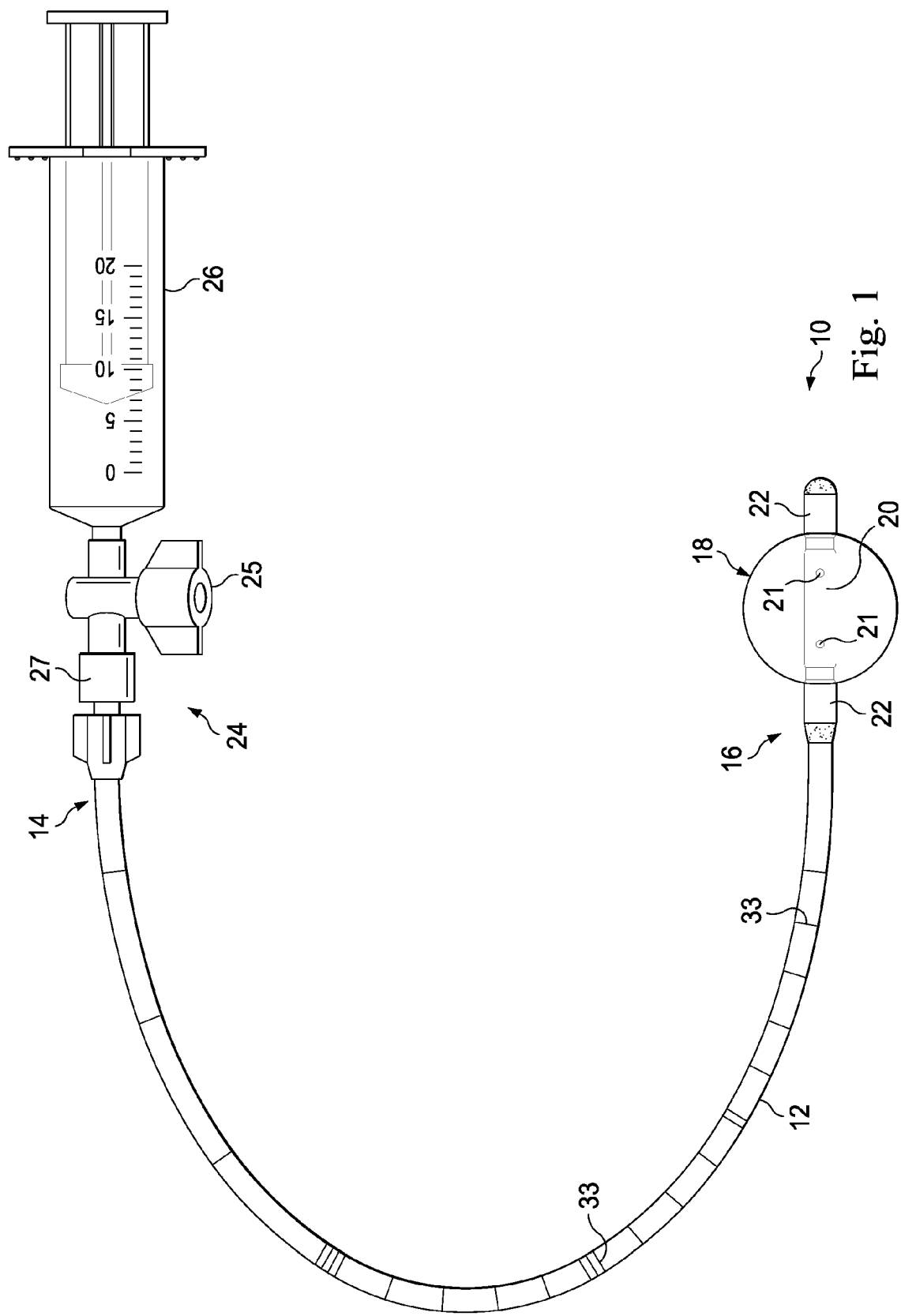
FIG. 1 illustrates a medical device for intervertebral disc assessment according to one embodiment of this disclosure.

The present disclosure relates generally to the field of intervertebral disc treatment, and more particularly to systems and methods for evaluating an intervertebral disc space in conjunction with a discectomy procedure. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein, are contemplated as would normally occur to one skilled in the art to which the disclosure relates.

Referring first to FIG. 1, a medical device for intervertebral disc assessment and treatment is indicated generally by the numeral 10. The device 10 includes a catheter 12 having a proximal end 14 and a distal end 16. An interior lumen (not shown) extends through the catheter between the ends 14, 16. An expandable body 18 is attached near the distal end 16 of the catheter 12. An inner catheter section 20 of catheter 12 is located between the proximal end 14 and the distal end 16 and extends through the expandable body 18. One or more openings 21 extend through a side wall of inner catheter section 20 and are in communication with the interior lumen of catheter 12. As shown more clearly in FIGS. 2 and 3, the expandable body 18 comprises an expandable tube 30 which extends around the inner catheter section 20. The expandable body 18 is secured to the catheter 12 using securing members 22.

The proximal end 14 of the catheter 12 carries a connection assembly 24 interconnecting the catheter with a material delivery instrument 26. A suitable material delivery instrument may be, for example, a syringe for containing an inflation medium to be delivered to the expandable body 18. The connection assembly 24 includes a two-way stopcock 25 and one or more luer lock connectors 27, and is configured to control the flow of the inflation medium between the material delivery instrument 26 and the catheter 12.

Suitable materials may be selected for the fabrication of the components of the disc assessment device 10. The catheter may have a shaft that is flexible and resistant to kink formation. The materials for the catheter may also be selected to facilitate advancement of the expandable body. The catheter can be constructed, for example, using standard flexible, medical grade plastic materials, like vinyl, nylon, polyethylenes, ionomer, polyurethane, and polyethylene tetraphthalate (PET). An elastomeric material, polyether block amide, which is offered by Arkema of Puteaux, France under the tradename Pebax may be suitable for some embodiments. The catheter can also be fabricated from more rigid materials to impart greater stiffness and thereby aid in its manipulation. More rigid materials that can be used for this purpose include stainless steel, nickel-titanium alloys, and other metal alloys.

The expandable tube may be formed of a highly compliant, elastomeric material capable of generally conforming to surrounding tissue when the expandable body 18 is inflated. Suitable materials may include silicone, latex, or neoprene. In some embodiments, a thermoplastic rubber elastomer offered by AdvanSource Biomaterial Corporation of Wilmington, Mass. under the tradename ChronoPrene may be particularly suitable. Alternatively, the expandable tube may be formed of a material, such as vinyl, nylon, or PET, having relatively inelastic properties.

To permit radiographic positioning of the expandable body 18, radiopaque markers 32 may be applied to the expandable body or the catheters. The markers 32 may be bands secured to the catheter 12 by crimping, swaging, or other techniques known in the art. A platinum-iridium alloy may be a suitable material for fabricating radiopaque markers. To aid in the positioning of the expandable body 18 without fluoroscopic guidance, distance markers 33 may be printed or otherwise formed on the catheter 12 to permit visual monitoring of the catheter insertion depth.

Figure 2:
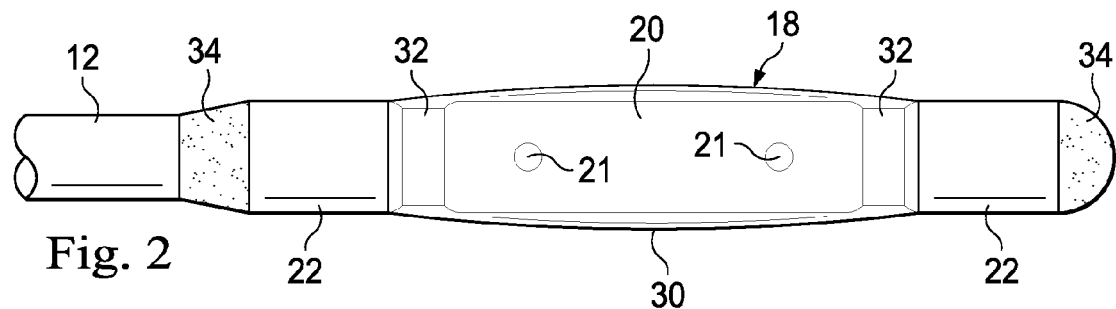
FIG. 2 illustrates a side view of a portion of the medical device of FIG. 1 in an unexpanded configuration.
Figure 3:
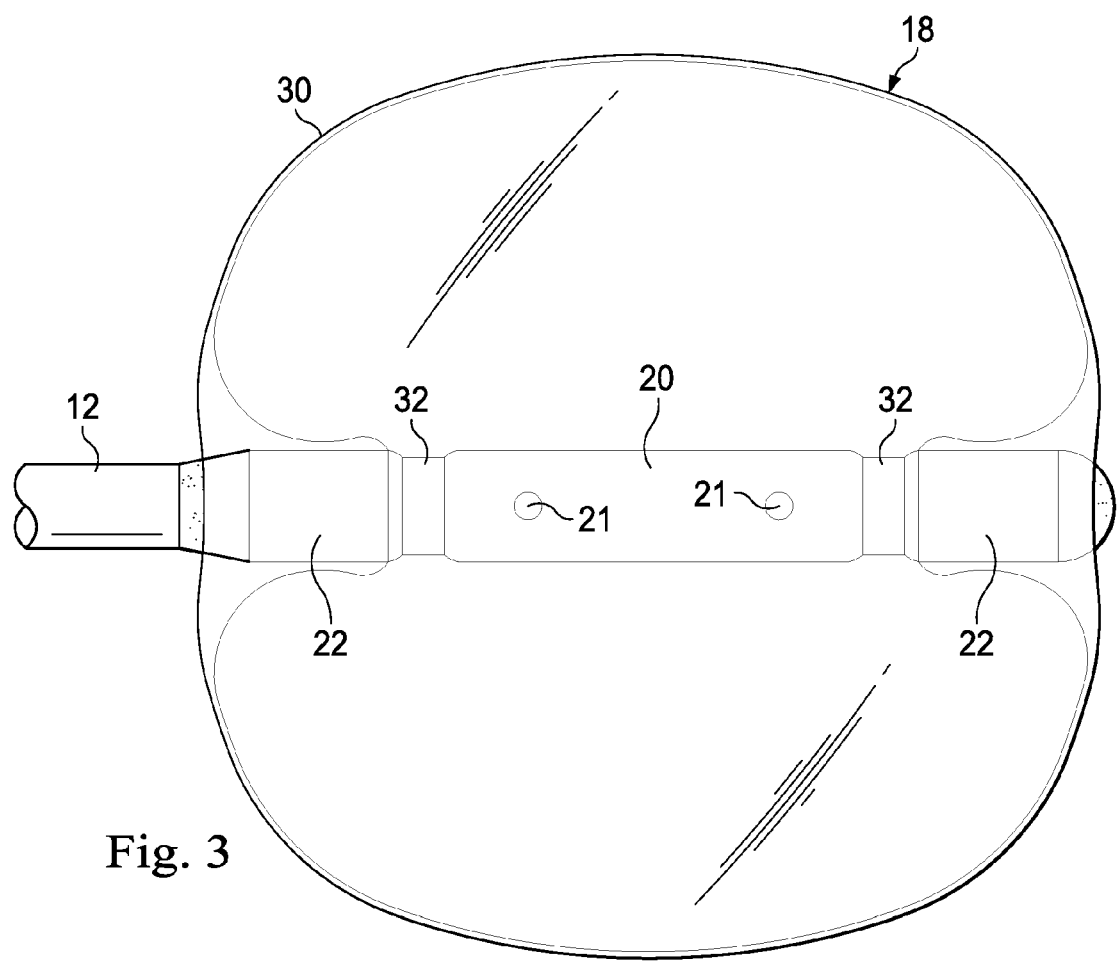
FIG. 3 illustrates a side view of a portion of the medical device of FIG. 1 in an expanded configuration.

As shown in greater detail at FIGS. 2 and 3, securing members 22 attach the expandable tube 30 to the catheter 12. The securing members 22 may be, for example, sections of heat shrinkable tubing which encircle and contact both the expandable tube 30 and the catheter 12. When heat is applied, to the heat shrinkable tubing, the tubing shrinks to tighten the expandable tube 30 against the catheter 12. The applied tubing maintains flexibility which allows it to elongate or otherwise deform when the expandable body is expanded, all the while maintaining a grip on the expandable tube and the catheter. Suitable heat shrinkable tubing may be medical-grade heat-shrinkable polyolefin tubing which includes an inner layer of adhesive. The heat-shrinkable tubing may include a modified polyolefin which has been cross linked by irradiation. Such tubing may be offered by Tyco Electronics Corporation of Berwyn, Pa. under the tradename Altera MT5000. In alternative embodiments, other forms of heat shrinkable material, including tape may be suitable. Applying the heat shrinkable tubing so that it overlaps both the expandable tube and the catheter may help prevent the expandable tube from slipping relative to the catheter, but in alternative embodiments, the heat shrinkable tubing may contact just the expandable tube. The use of heat shrinkable material may be particularly useful when used with expandable tubes or catheters formed of materials that are resistant to conventional forms of attachment such as laser bonding, thermal bonding, adhesives, or coextrusion. Alternatively, the heat shrinkable material may be used to supplement these or other forms of attachment.

Although the securing members 22 may be used alone to secure the catheter 12 to the expandable tube 30, additional bonding material may provide greater adherence. The use of a medical grade adhesive 34 may be used to further promote adherence of the expandable tube 30 to the catheters. A ring of adhesive 34 applied at the opposite ends of the tube 30 at the base of the securing mechanisms 22 may prevent slipping of the shrink tubing along the catheters 12, 20. Suitable medical grade adhesive may include biocompatible products that cure in the presence of ultraviolet light.

In alternative embodiments, adhesive, including ultraviolet adhesive, may be used without a securing member 22 to adhere the expandable tube to the catheters. In still another alternative, the securing member may be formed of a radiopaque material, including a radiopaque shrink tubing, to supplement or eliminate the need for the radiopaque markers.

Figure 4:
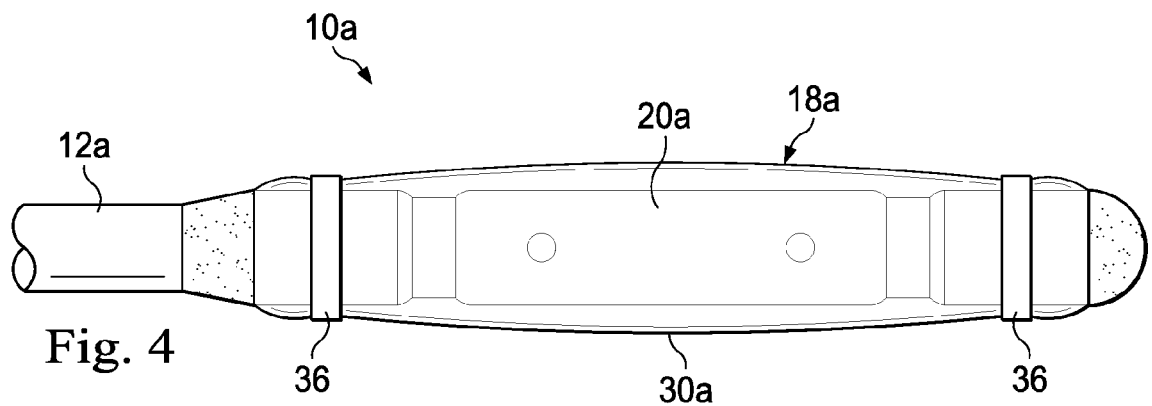
FIG. 4 illustrates a side view of a portion of a medical device according to an alternative embodiment of this disclosure.

As shown in FIG. 4, an alternative medical device 10a may be substantially similar to medical device 10 described above, but may include the differences to be described. The device 10a may include a catheter 12a which carries an expandable body 18a. An expandable tube 30a is attached to catheter 12a by securing members 36 which may be a wire band. The band may be crimped, swaged, or otherwise tightened to secure the expandable tube to the catheters. In alternative embodiments, other types of external gripping devices including rings, wires, ties, and clamps may be used to apply an external gripping force to hold the expandable tube to the catheters. In further alternative embodiments, the catheter may include a feature such as a protruding ridge or a recessed channel which may engage the securing member to promote adherence between the catheter and the expandable tube and to limit the expandable tube from slipping relative to the catheter.

Figure 5:
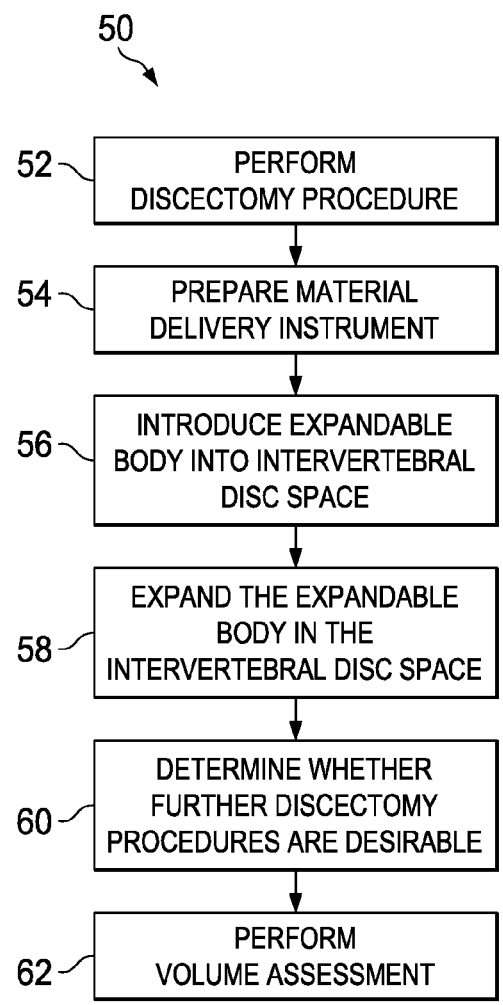
FIG. 5 describes a surgical method according to one embodiment of this disclosure.

As described in FIG. 5, the device 10 may be used by a practitioner to assess space within an intervertebral disc according to the method 50. At step 52, a conventional discectomy procedure may be performed to remove all or a portion of a nucleus pulposus from an intervertebral disc space D located between vertebral bodies V1 and V2 (FIG. 6). To determine if further discectomy is needed and to determine the location for any additional discectomy, the disc assessment device 10 may be used.

At step 54, the material delivery instrument 26 may be prepared. For example, the material delivery instrument may be an empty 20 cc locking syringe with a non-rotating male luer lock. This may be attached to the connection assembly 24 which in this embodiment includes a two-way stopcock and a luer connection. Optionally, the expandable body 18 and catheter 12 may be vacuumed prior to use to eliminate or minimize air bubbles when inflation medium is later added. The stopcock may be used to retain the vacuum in the expandable body and catheter while the syringe is detached and filled with an inflation medium such as radiopaque contrast media. The syringe is then reattached to the stopcock.

At step 56, the expandable body 18 and catheter 12 may be introduced into a cannula 70 which provides access to the intervertebral disc space D located between vertebral bodies V1 and V2. In this embodiment, a percutaneous and unilateral access technique is used, but in alternative embodiments an open procedure or multilateral approach may be used. The placement of the expandable body 18 and the catheter 12 may be guided by fluoroscopy.

At step 58, the expandable body 18 is gradually inflated under fluoroscopy using radiopaque contrast media. The practitioner may detect increasing resistance to inflation as the expandable body 18 expands and may stop further inflation when the expandable body 18 contacts the tissue remaining in the disc space D after the discectomy.

As shown in FIG. 3, the securing members 22 may securely hold the expandable body 18 on the catheters 12, 20 when the expandable body is inflated. When formed from resilient material, as shown in FIG. 3, the securing members 22 may permit limited stretching, folding, deformation, or other reconfiguration that permit the securing member to adapt to the changing shape of the expandable body.

At step 60, the practitioner may assess whether further discectomy is necessary. Under fluoroscopy, the practitioner may determine whether the sufficient discectomy has been performed by determining whether the expandable body 18, in the inflated condition, contacts the endplates of the superior and inferior vertebral bodies and whether the expandable body has inflated past the midline of the contralateral portion of the disc. The discectomy and assessment procedures may be repeated until the practitioner is satisfied with the extent of discectomy.

At step 62, after final assessment is performed, the practitioner may compare the initial volume of the inflation media in the material delivery instrument 26 prior to expansion with the final volume of the inflation media in the material delivery instrument after expansion. The difference in volumes can be used to provide a volumetric estimate of the extent of the discectomy procedure which can be used to determine the amount of bone graft or other filling material to be implanted for fusion.

It is understood that the device 10 is not limited to use within an intervertebral disc space, but could be used to create, treat, or assess cavities in other regions of a body including regions within vasculature, organs, other soft tissue, or bone, including a vertebral body.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept. In the claims, means-plus-function clauses are intended to cover the structures described herein as performing the recited function and not only structural equivalents, but also equivalent structures.

What is claimed is:

1. A system for assessing an intervertebral disc space comprising:
    an elongated catheter with proximal and distal ends;
    an expandable body attached to the proximal and distal ends of the elongated catheter, the expandable body including proximal and distal end portions; and
    a first securing mechanism attached to a proximal end portion of the expandable body and a second securing mechanism attached to a distal end portion of the expandable body;
    wherein the first and second securing mechanisms each increase in length when the expandable body is in an inflated state.

2. The system of claim 1 wherein the first securing mechanism encircles the proximal end portion of the expandable body and a second securing mechanism encircles the distal end portion of the expandable body.

3. The system of claim 2 wherein the first and second securing mechanisms each having a first length along the catheter when the expandable body is in an inflated state and deform to have an increased second length along the catheter when the expandable body is in an inflated state.

4. The system of claim 3 further comprising a bonding material disposed at a base portion of each of the first and second securing mechanisms to prevent the first and second securing mechanisms from slipping along the catheter.

5. The system of claim 1 wherein the securing mechanism directly contacts both the expandable body and the catheter.

6. The system of claim 1 wherein the securing mechanism directly contacts only the expandable body.

7. The system of claim 1 wherein the securing mechanism comprises a heat shrinkable tube.

8. The system of claim 1 wherein the securing mechanism comprises polyolefin.

9. The system of claim 1 wherein the securing mechanism comprises an adhesive tape.

10. A surgical system comprising:
    a catheter;
    a balloon comprising a first end that is coupled to a first portion of the catheter and a second end that is coupled to a second portion of the catheter;
    a first securing mechanism attached to the first end to secure the first end to the first portion; and
    a second securing mechanism attached to second end to secure the second end to the second portion,
    wherein the securing mechanisms each increase in length as the balloon moves from an uninflated configuration to an inflated configuration.

11. The system of claim 10 wherein the catheter is flexible.

12. The system of claim 10 wherein the securing mechanisms each comprise heat shrinkable tubing.

13. The system of claim 10 wherein the securing mechanisms each comprise heat-shrinkable polyolefin tubing which includes an inner layer of adhesive.

14. The system of claim 10 wherein the securing mechanisms each comprise a modified polyolefin which has been cross linked by irradiation.

15. The system of claim 10 wherein the securing mechanisms each overlap the balloon and the catheter.

16. A surgical system comprising:
    a catheter;
    a balloon comprising a first end that is coupled to a first portion of the catheter and a second end that is coupled to a second portion of the catheter;
    a first securing mechanism encircling the first end to secure the first end to the first portion; and
    a second securing mechanism encircling the second end to secure the second end to the second portion,
    wherein the securing mechanisms each increase in length as the balloon moves from an uninflated configuration to an inflated configuration.

17. The system of claim 16 wherein adhesive is applied at the first and second ends and at a base of each of the securing mechanisms to prevent slipping of the securing mechanisms along the catheter.

18. The system of claim 16 wherein the securing mechanisms each comprise heat shrinkable tubing.

19. The system of claim 16 wherein the securing mechanisms each comprise heat-shrinkable polyolefin tubing which includes an inner layer of adhesive.

20. The system of claim 16 wherein the securing mechanisms each overlap the balloon and the catheter.

* * * * *